United States Patent [19]

Duffin

[11] Patent Number: 5,133,350

[45] Date of Patent: Jul. 28, 1992

[54] MODE SWITCHING PACEMAKER

[75] Inventor: Edwin G. Duffin, New Brighton, Minn.

[73] Assignee: Medtronic, Inc., Minneapolis, Minn.

[21] Appl. No.: 648,469

[22] Filed: Jan. 31, 1991

[51] Int. Cl.⁵ .............................................. A61N 1/36
[52] U.S. Cl. ...................... 128/419 PG; 128/419 PT
[58] Field of Search .................. 128/419 PG, 419 PT, 128/419 D

[56] References Cited

U.S. PATENT DOCUMENTS

| | | | |
|---|---|---|---|
| 3,999,557 | 12/1976 | Citron et al. | 128/419 PG |
| 4,163,451 | 8/1979 | Lesnick et al. | 128/419 PG |
| 4,312,355 | 1/1982 | Funke | 128/419 PG |
| 4,363,325 | 12/1982 | Roline et al. | 128/419 PG |
| 4,393,874 | 7/1983 | Nappholz et al. | 128/703 |
| 4,548,209 | 10/1985 | Wielders et al. | 128/419 D |
| 4,577,633 | 5/1986 | Berkovits et al. | 128/419 PG |
| 4,932,406 | 6/1990 | Berkovits | 128/419 PG |

OTHER PUBLICATIONS

"The NASPE/BPEG** Generic Pacemaker Code for Antibradyarrhythmia and Adaptive-Rate Pacing and Antitachyarrhythmia Devices" by Bernstein, et al., PACE, vol. 10, Jul.-Aug. 1987 Part I.

"Long-Term Pacing in Sinus Node Disease: Effects of Stimulation Mode on Cardiovascular Morbidity and Mortality", by Rosenqvist et al. American Heart Journal-16(1): Jul. 16-22, 1988.

*Primary Examiner*—Francis Jaworski
*Assistant Examiner*—George Manuel
*Attorney, Agent, or Firm*—Reed A. Duthler; Harold R. Patton

[57] ABSTRACT

A mode switching bradycardia pacemaker especially adapted for incorporation in an antitachyarrhythmia pacing and/or cardioversion/defibrillation system, provides AAI pacing in the absence of an intrinsic atrial rate exceeding the pacing lower rate and as long as the patient's heart is capable of normal AV conduction. The pacemaker switches to VVI mode any time that the patient's ventricular rate falls below a predetermined value. The mode switching may be implemented in a DDD pacing system or in a pacing system employing an atrial and ventricular sense amplifier and a single pacing output circuit and switching circuitry for switching its output between atrial and ventricular leads. This bimodal operation allows use of AAI pacing for the antiarrhythmic and hemodynamic benefits of maintaining atrial function in patients with sinus node disease, by obviates the risk of ventricular asystole should the AAI mode become ineffective due to transiant or newly evolving permanent impairment of AV conduction in those patients where atrial synchronous tracking is considered undesirable. In the AAI/VVI bimodal operation, only a single chamber of the patient's heart is paced at any given time, AAI pacing occurs in the presence of spontaneous or conducted ventricular depolarization, and VVI pacing is resorted to in AV dissociation or in the absence of a ventricular rhythm exceeding the lower pacing rate.

17 Claims, 6 Drawing Sheets

MODE SWITCHING PACEMAKER

BACKGROUND OF THE INVENTION

1. Field of the Invention

This invention relates to cardiac pacemakers, and particularly pacemakers which provide limited bimodal fixed rate pacing for certain patients.

2. Description of the Prior Art

Commonly assigned U.S. Pat. No. 4,932,406, incorporated herein by reference, sets forth the prior art of single and dual chamber pacing and physiologic sensor based rate responsive pacing. Dual chamber DDD physiologic pacemakers following the teachings of U.S. Pat. No. 4,312,355 to Funke may be characterized as possessing a number of different pacing modes which are switched in or out of operation in the presence or absence of atrial and ventricular sensed events. Such DDD pacemakers are constantly updating their functional modes at the end of programmed escape intervals or upon earlier occurring atrial and ventricular events. However, DDD pacemakers do not switch modes in the sense that the expression has been defined in the art.

"Mode switching" connotes a semi-permanent mode change driven by sensed heart activity and/or physiologic sensor derived events occurring in a first relationship wherein the device dictates that it remain in the mode it is operating in until those events assume a second defined relationship. For example, one of the earliest mode switching devices is illustrated by pacemakers exhibiting hysteresis and particularly pacemakers of the type described in U.S. Pat. No. 4,363,325 to Roline, et al, and U.S. Pat. No. 3,999,557 to Citron. In the '325 patent, a pacemaker capable of operating in the atrial synchronous ventricular inhibited (VDD) mode automatically switches to the VVI mode at a preset atrial sensed driven upper rate. The mode is switched back to VDD when a lower atrial sensed driven rate is detected. In the '557 patent, a VVI pacemaker remains "off" until a bout of extreme bradycardia (a heart rate less than 30 bpm) is detected, whereupon the VVI pacemaker switches "on" at a lower rate of 70 bpm, for example. Thereafter, the pacemaker remains in the VVI mode.

Contemporaneously with the introduction of dual chamber pacing, particularly DDD pacing, single chamber and subseguently dual chamber rate responsive pacemakers were developed as described in the aforementioned application. With the introduction and incorporation of physiologic sensors into single and dual chamber pacemakers, a four letter code denoting the modes o operation of pacemakers with and without physiologic sensors and rate adaptive pacing capabilities was published in "The NASPE/BPEG Pacemaker Code" by Berstein, et al, PACE, 10 (4), July–August, 1987, which updated the three-letter code published in the American Journal of Cardiology, 34:487 (1974). The incorporation of physiologic sensors added impetus to the acceptance of the "mode switching" vernacular. However, mode switching is still applied to pacing systems which operate in more than one of the recognized modes in a semi permanent manner as described above.

Current physiologic pacing systems, whether incorporating physiologic sensors of the body's need for oxygen or not, almost always include the components of a DDD pacing system where the preferred mode of operation is to provide atrial and synchronous ventricular stimulation as needed at a rate that varies between a programmed lower pacing rate and upper pacing rate. The advantages of DDD pacing in patients who have a relatively normal SA node function in response to exercise and who do not suffer recurrent episodes of atrial or ventricular tachycardia are well known. However, when such patients suffer episodes of atrial tachycardia and the pacemaker functions at its upper rate limit, cardiac output may decrease and the patient may become distressed. Additionally, there is a certain danger of inducing ventricular tachycardias in response to sustained operation at the pacing upper rate limit.

Furthermore, in such patients it may be desirable to implant a tachyarrhythmia control device in conjunction with bradycardia pacing capabilities wherein it is necessary to monitor the electrocardiogram to detect the herald signs or the onset of ventricular tachycardia or fibrillation. The operation of the bradycardia pacemaker at the upper rate limit involves the blanking of the sense amplifiers on and off at the upper pacing rate which may make it difficult to detect a developing arrhythmia. Nevertheless, it is desirable to provide some form of backup pacing to treat bradycardia to support patients whose hearts' condition may induce either bradycardia or tachycardia. Consequently, such tachyarrhythmia control devices have provided for at least single chamber fixed rate bradycardia pacing and DDD pacing has been suggested for inclusion in such systems as set forth, for example, in commonly assigned U.S. Pat. No. 4,548,209 to Wielders, et al. Moreover, it has been recognized that it would be desirable in such tachycardia control systems to include both atrial and ventricular sensing in order to discriminate atrial and ventricular tachycardias and particularly to assist in the discrimination between sinus tachycardias and unstable ventricular tachycardias which may degenerate into life-threatening ventricular fibrillation as described, for example, in my commonly assigned co-pending U.S. Pat. application Ser. No. 07/621,133 filed Nov. 30, 1990.

Finally, in such tachyarrhythmia control devices, antitachycardia pacing therapies are provided which require at least one pacing energy output pulse generator and timing and control circuitry to trigger adaptive or burst overdrive trigger signals.

SUMMARY OF THE INVENTION

Accordingly, it is an object of the present invention to provide a bradycardia pacing system which provides atrial and ventricular demand pacing in support of patients whose underlying heart rhythms are insufficient in both the atrium and the ventricle on certain occasions.

It is furthermore an object of the present invention to provide atrial demand pacing preferably and to switch to ventricular demand pacing in the absence of AV conduction of the estimulated or sensed atrial event and in the absence of an underlying ventricular rhythm (independent of the atrium) exceeding the pacing lower rate.

These and other objects of the present invention are realized in the method and apparatus for operating a bradycardia pacemaker to provide demand pacing at a lower rate in either the atrium or the ventricle, depending upon the presence or absence of ventricular, depending upon the presence or absence of ventricular sensed events recurring within a predetermined ventricular escape interval. More particularly, the present invention contemplates providing atrial demand pacing at a predetermined atrial lower rate escape interval as long as ventricular events are sensed within the ventricular escape interval and switching modes to provide ventricular demand pacing an inhibit atrial demand pacing in the event that the ventricular escape interval times out without an intervening sensed ventricular event.

In the system of the present invention, the detection of any ventricular event within the ventricular escape interval switches the pacing mode back to the atrial demand mode. While in the atrial demand mode, the ventricular escape intervals continue to be timed out, whereas while in the ventricular demand mode, the atrial escape interval counters and sense amplifier are turned off.

The ventricular demand pacing mode operates with hysteresis: in the atrial demand mode, the ventricular escape interval is prolonged to bias the continued operation of the pacing system in favor of the atrial demand mode, while assuring that ventricular pacing occurs should an excessive time pass with no ventricular activity having occurred. In this fashion, the triggered depolarization of the atrium and the natural depolarization of the ventricle is encouraged to provide maximal cardiac output and the other benefits of AAI pacing set forth in the article, "Long term Pacing in Sinus Node Disease: Effects of Stimulation Mode on Cardiovascular Morbidity and Mortality," by M. Rosenguist et al, *Am. Heart Journal*, 116(1):16–22, July 1988.

These and other advantages and features of the present invention will be apparent from the following description of the accompanying drawings which illustrate preferred embodiments exemplifying the best modes of carrying out the invention as presently perceived.

BRIEF DESCRIPTION OF THE DRAWINGS

Reference is now made to the accompanying detailed drawings of the preferred embodiments in which like reference numerals represent like or similar parts throughout, and wherein.

DESCRIPTION OF THE PREFERRED EMBODIMENTS

Hardware suitable for practicing the present invention includes the Medtronic Dysrhythmia Research Instrument which is available from Medtronic, Inc., Fridley, Minnesota. This machine is a computer base physiologic stimulator operating under the control of software. The computer hardware is interfaced with the heart through atrial and ventricular sense amplifiers and atrial and ventricular pulse generators. U.S. Pat. No. 4,577,633, which is incorporated herein by reference, describes the computer driven stimulator and its programmable functions in more detail.

Figure 1:
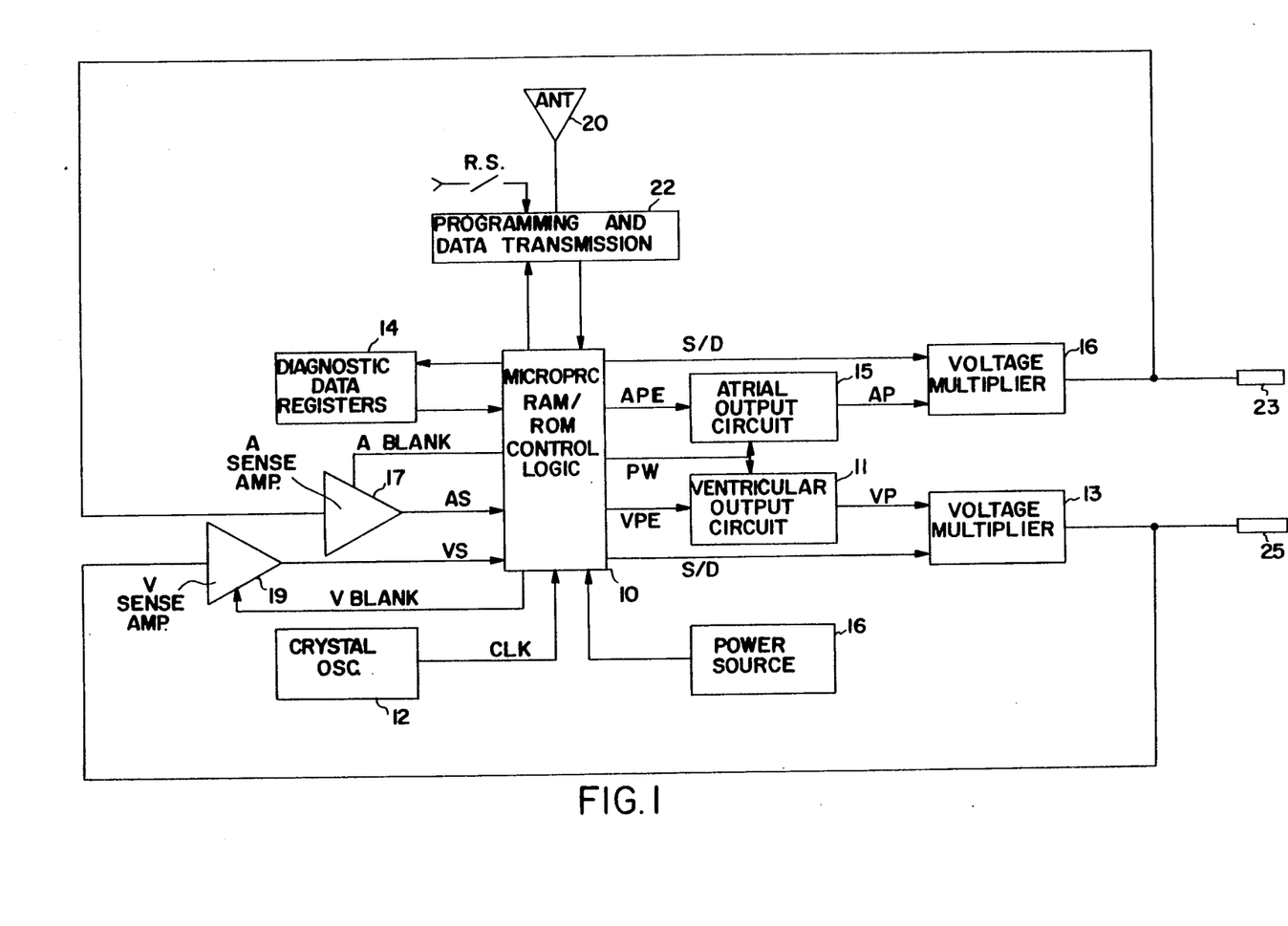
FIG. 1 is a simplified block diagram of the bimodal pacing system of the present invention.
Figure 2:
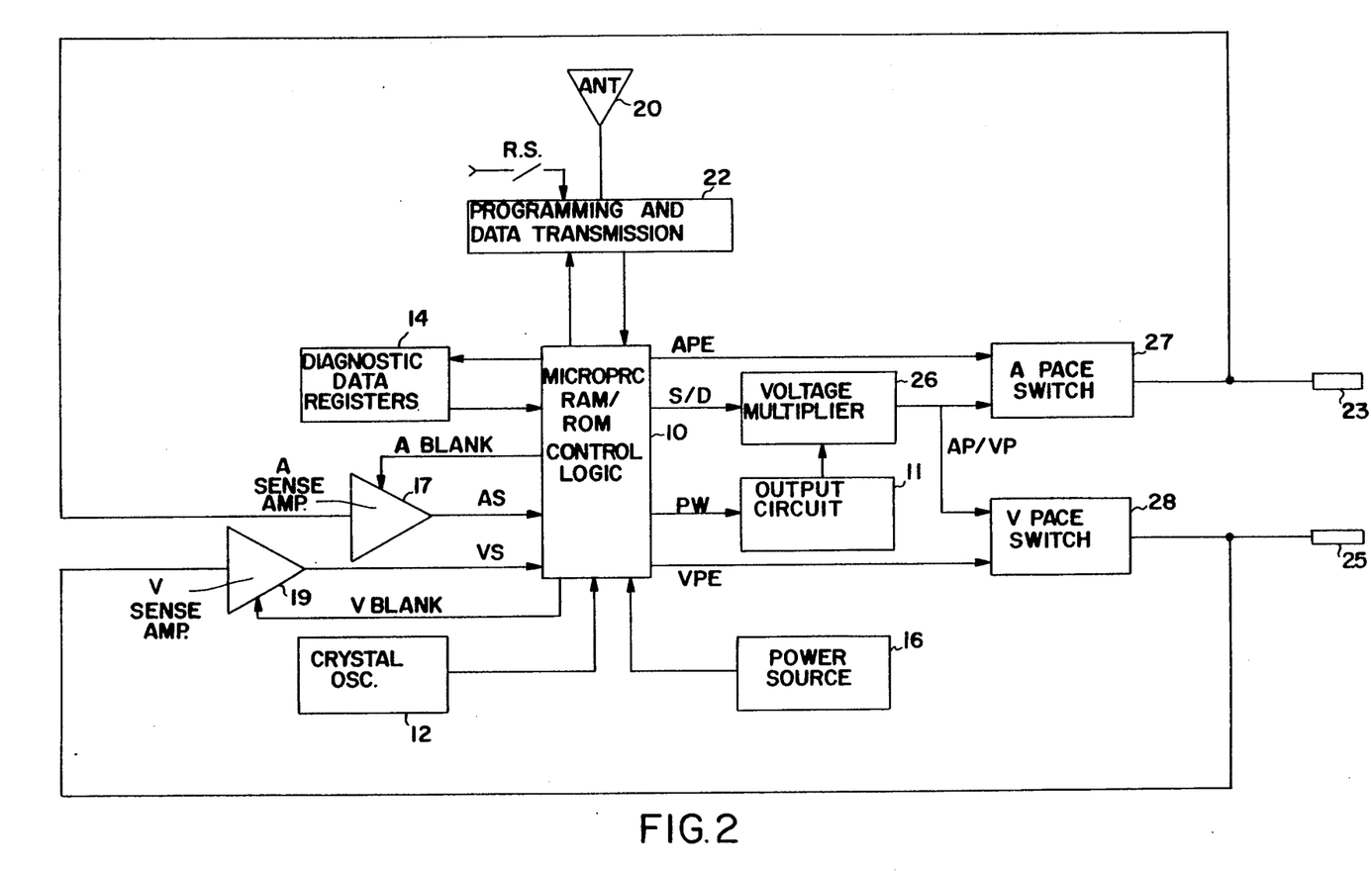
FIG. 2 is a further embodiment of the simplified block diagram of the bimodal pacing system of the present invention.

Referring now to FIGS. 1 and 2, they depict simplified block diagrams of the bimodal pacing system of the present invention embodied in a bradycardia pacemaker. FIG. 1 includes the major components of a DDD pacemaker, such as a Medtronic Symbios ® or Elite ® pacemaker, which includes separate atrial and ventricular output circuits, whereas FIG. 2 depicts a second embodiment where single output circuit and voltage multiplier circuit is mulitplexed between atrial and ventricular pacing channels, depending on the mode of operation at the time.

Both embodiments of FIGS. 1 and 2 include a digital logic and/or microprocessor based control logic block 10 (including onboard RAM and ROM memory and a central processing unit, in the microprocessor base system). Those major components further include a crystal oscillator 12, diagnostic data registers 14, power source 16, antenna 20, reed switch R.S., programming and data transmission block 22, and the atrial and ventricular input sense amplifiers 17 and 19 coupled to respective atrial and ventricular electrodes 23 and 25 adapted to be positioned in the atrium and ventricle of the heart.

In reference to FIG. 1, separate atrial and ventricular output circuits 15 and 11 are coupled through respective voltage multiplier circuits 16 and 13 to the respective atrial and ventricular output electrodes 23 and 25. The control logic block 10 develops atrial pace enable (APE), ventricular pace enable (VPE), pulse width (PW), and single/double (S/D) control signals which are applied as depicted to the blocks 15, 11, 16, 13, in a manner to be described hereinafter in order to provide atrial or ventricular stimulation in the AAI or VVI pacing modes. The logic block 10 times out the A-A and V-V escape intervals, and depending upon the pacing mode apply the atrial and ventricular pacing stimulation output pulses to the atrium or the ventricle of the patient's heart.

At the time that pacing pulses are delivered, the atrial and ventricular sense amplifiers 17, 19, are blanked by A blank and V blank signals. At other times, the atrial sense amp 17 provides the atrial sense (AS) signal to the block 10 and the ventricular sense amplifier 19 provides the ventricular sense (VS) signal to the logic block 10 to reset or start escape intervals in the manner to be described hereinafter. The logic block 10 provides other refractory and sensitivity signals for controlling the processing of the AS and VS signals in a manner well known in the art.

Turning to FIG. 2, in the second embodiment of the invention, it is contemplated that a single output circuit 11 and voltage multiplier 26 may be employed with atrial and ventricular pacing switches 27 and 28 under the control of the signals PW, S/D, APE and VPE to supply atrial or ventricular stimulating pulses to the atrial and ventricular electrodes 23, 25. The embodiment of FIG. 2 is somewhat more specialized than the embodiment of FIG. 1. In the FIG. 1 embodiment, it may be contemplated that the logic control block 10 may be programmed by appropriate programming instructions to operate in a number of potential modes, including the modes of the invention as well as prior art modes, depending upon the patient's condition at the time of programming. Consequently, the bimodal switching operations contemplated by the present invention may be employed as either the only available modes of operation or as one set of modes in an otherwise widely programmable DDD pacing system.

In accordance with the present invention, it is contemplated that in certain patients, it is desirable to provide either atrial demand or ventricular demand pacing, depending upon a patient's underlying ventricular rhythm and the ability of the heart to conduct atrial depolarizations to the ventricle.

As explained in the aforementioned Rosenguist et al article, in sinus node disease patients with implanted VVI and AAI pacemakers and who were followed for up to four years after initial implant, the incidence of permanent atrial fibrillation and congestive heart failure was significantly higher in the patients with VVI pacemakers than in the patients with AAI pacemakers. The authors conclude that AAI pacing results in beneficial effect on mortality as compared with VVI pacing.

The bimodal AAI/VVI operation of the present invention contemplates switching between the AAI and VVI modes in dependence upon the presence or absence of such spontaneous ventricular depolarizations (referred to as premature ventricular contractions or PVC's) or triggered ventricular depolarizations resulting from a previous atrial natural or triggered depolarization. A preferred mode for accomplishing such mode switching is set forth in the AAI/VVI mode control flow diagram of FIG. 3 in conjunction with the simplified block diagram of FIG. 4 and the wave form diagram of FIG. 5. This bimodal operation in the simplified block diagram of FIG. 4 may be incorporated within the bradycardia pacing system of FIGS. 1 and 2, as well as in the more comprehensive bradycardia pacing and antitachycardia control device of FIG. 6.

Figure 3:
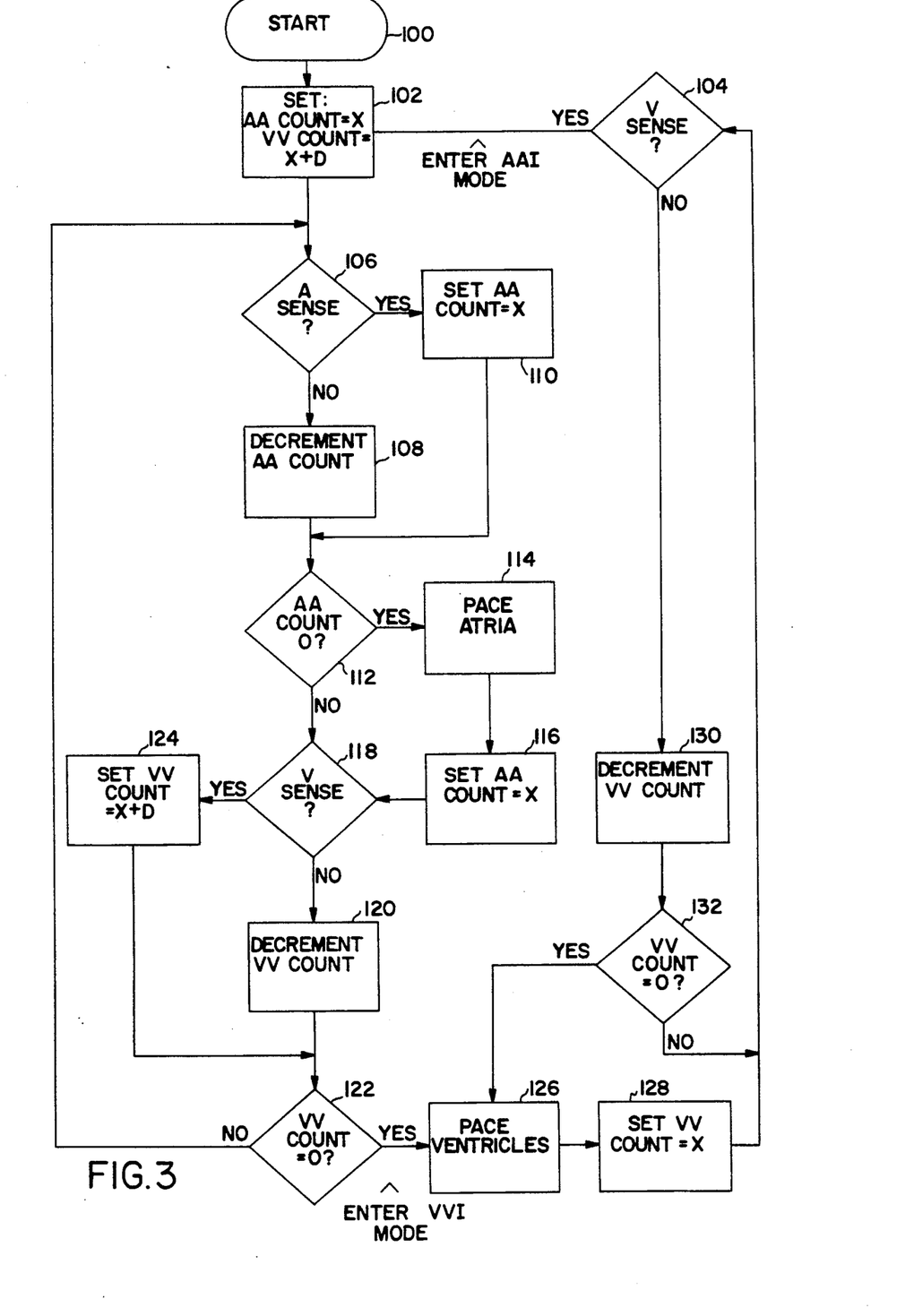
FIG. 3 is a flow chart of the AAI/VVI mode control algorithm of the present invention.
Figure 4:
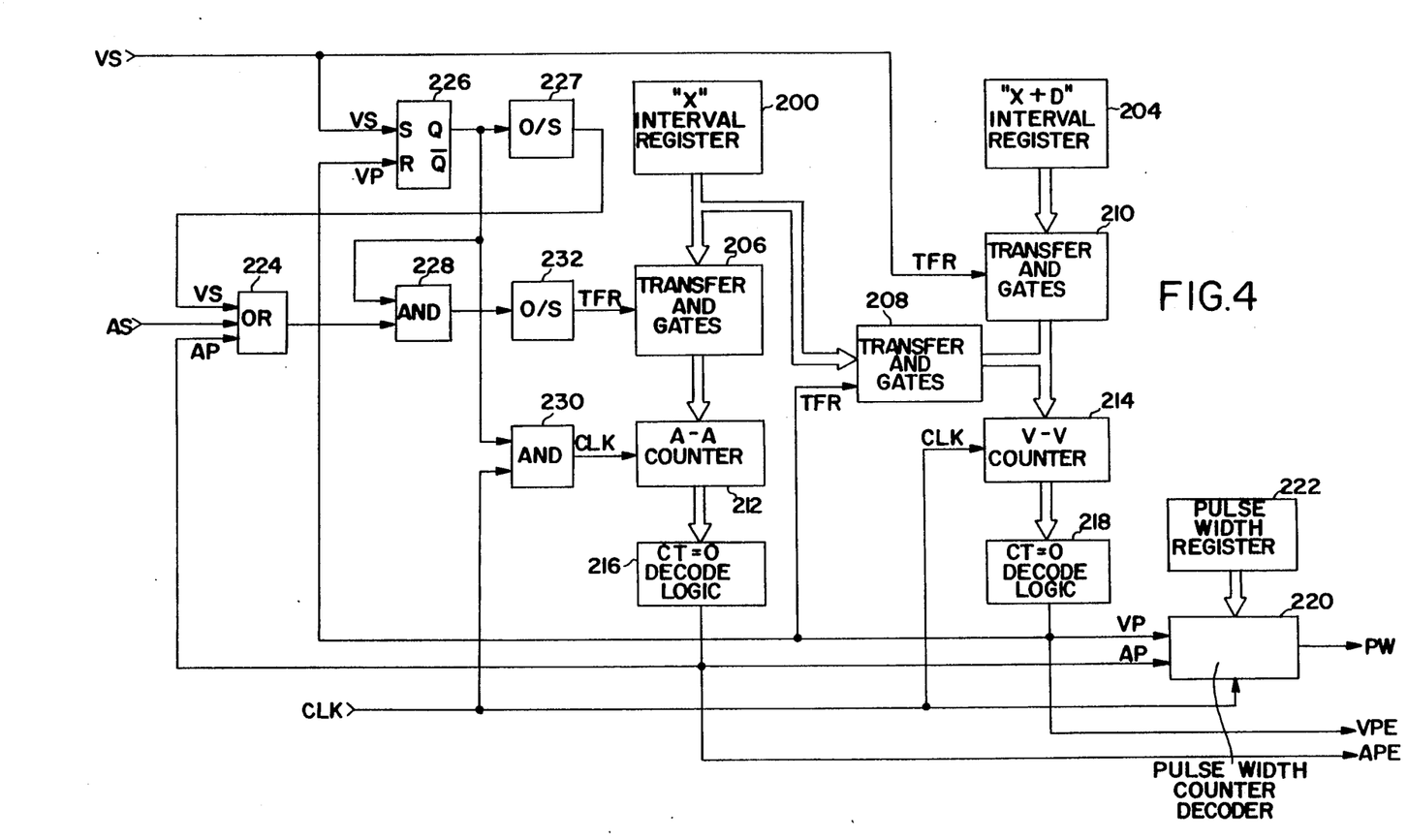
FIG. 4 is a simplified block diagram of a logic and counter system for implementing the AAI/VVI mode control algorithm of FIG. 3 within the systems depicted in FIGS. 1 and 2.

Turning now to FIG. 3, the AAI/VVI mode control diagram depicts the steps which may be accomplished either in software in a microprocessor based system or in digital logic hardware of the type depicted in FIG. 4. In FIG. 3, at START block 100, the program is initiated by first setting the A-A count equal to X and the V V count egual to X+D in block 102. Thus, the A-A counter is set to a value which is less than the value of the V-V counter and both counters are designed to count down to zero, whereupon an atrial pace event or a ventricular pace event will be initiated. In accordance with the present invention, the presence of a ventricular sense event in block 104 will reset both counters and switch the pacing mode to the AAI mode until such time as the V-V counter times out whereupon the mode is switched to the VVI mode.

Figure 5:
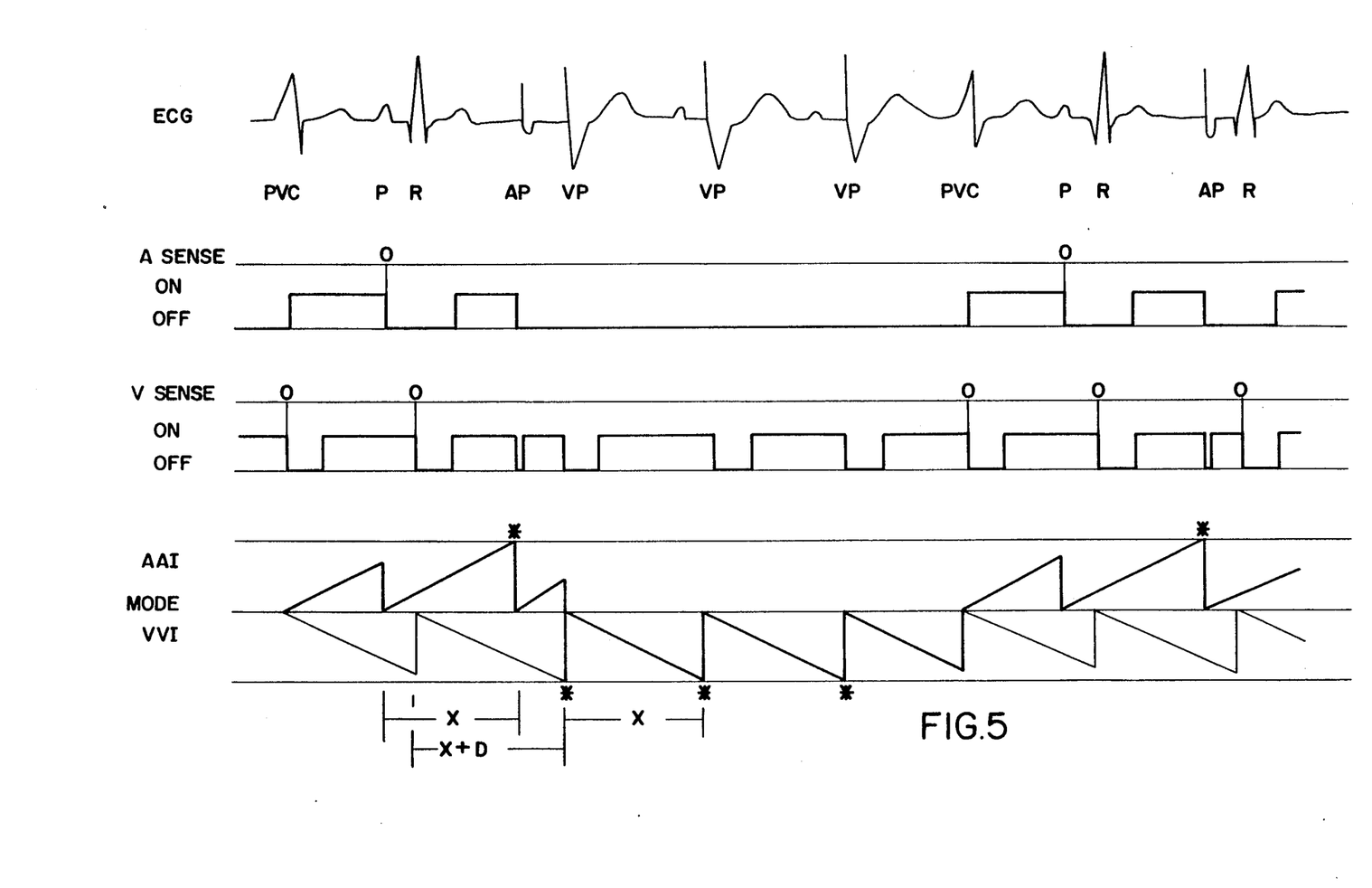
FIG. 5 is a wave form diagram of the operation of the AAI/VVI mode control flow chart of FIG. 3 and block diagram of FIG. 4.

In reference to FIG. 5, such a transition between modes is shown in the lowest wave form diagram designated "MODE" which depicts both the controlling pacing mode as well as the timing out of the A-A and V-V counters. The ECG wave form at the top of FIG. 5 depicts natural depolarization events as well as triggered or paced events which are labeled accordingly. As shown in the MODE wave form at the bottom of FIG. 5, the escape intervals for the A-A and V-V counters are depicted as X and X+D. As long as the AAI mode controls, the ventricular escape interval is set to X+D and the atrial escape interval is set to X. However, when the mode switches to the VVI mode, the ventricular escape interval is also set to X. In this fashion, a form of hysteresis is built in to bias the operation toward the AAI mode.

The transition from the AAI mode to the VVI mode (as depicted in FIG. 5) takes place at the time-out of the VVI X+D escape interval, which signifies that the ventricles have been inactive for an excessive time period. As shown in the first complex labeled "PVC," both the AA and VV escape intervals are restarted in response to this first VS event. This PVC induced VS event initiates AAI pacing, whereas VS events occurring while in the AAI mode do not reset the AA escape interval.

Returning to FIG. 3, the setting of the A-A counter to X and the V-V counter to X+D commences the countdown of both counters by a fixed frequency clock. During the countdown, the atrial sense and ventricular sense inputs are monitored in blocks 106, 104 and 118. Initially, if an AS event is not detected (which would be expected), the A-A counter count is decremented in block 108. If an AS event is detected, the decision block 106 commands block 110 to set the A-A count back to X in block 110. In the normal course of events, it would be expected that the atrial event or P-wave would occur prior to a ventricular event or R-wave. Consequently, the count in the A-A counter continues to be decremented until it reaches zero. During that time, the V-V counter is simultaneously being decremented as shown in block 120.

Assuming that the A-A counter counts out before any AS event or VS event is detected, then the decision block 112 commands block 114 to pace the atria and in turn to set the A-A counter back to X in block 116 and return to the V sense decision block 118. The resetting of the A-A counter to X does not affect the count in the V V counter and it continues to be decremented in block 120 until either a VS event occurs or the V-V counter count reaches zero in block 122. If a VS event occurs prior to the V-V counter reaching zero, then the VS decision block 118 commands block 124 to reset the V-V counter to X+D. So long as the V-V counter count does not egual zero, the decision block 122 loops back to the A sense block 106. Thus, in the primary loop comprising blocks 106 to 124, the pacemaker is operating in the AAI mode wherein only atrial pacing takes place in the event that the A-A countercount reaches zero.

Turning to FIG. 5, pacing in the AAI mode and the transition to the VVI mode and from the VVI mode back to the AAI mode are depicted. In the AAI mode, the pacemaker sense amplifier is "on" except for blanking and refractory intervals after delivery of or the sensing of an atrial or a ventricular event. However, at other times when the VVI mode is controlling, the atrial sense amplifier is completely disabled.

The ventricular sense amplifier, on the other hand, is enabled at all times except during blanking and refractory periods in order to effect the switchover to the VVI mode in the event that the V-V escape interval times out.

Returning to FIG. 3, the timing out of the V-V counter in decision block 122 commands the pacing of the ventricle in block 126 and the setting of the V-V count to X in block 128. The operation of block 122 and 128 is such that the A sense decision block 106 is not enabled and, in the VVI mode, the decision blocks including blocks 104, 122 and 126 to 132 control. Once the V V counter is set to X, the program loops back to the V sense decision block 104 and to the decrement V-V count block 130 in the absence of an intervening ventricular event. In the VVI mode, the V V counter count is decremented to block 130 until either a VS event occurs (whereupon the device switches back to the AAI mode by virtue of the operation of decision block 104, block 102) or the V-V counter count reaches zero. When the V-V count reaches zero, decision 132 commands block 126 to initiate a VP event and to reset the V-V counter count to X and continue to monitor for VS events and decrement V-V counter.

Returning to FIG. 5, the switching of the pacing mode back to the AAI mode is depicted at the occurrence of the PVC constituting the sixth ventricular ECG complex. At that transition point, it will be noted that the V V counter escape interval X had not timed out. It will also be noted that the next or seventh ECG complex comprises the natural P-wave and R wave which reset both the A-A and the V V escape interval counters and the pacing mode remains in the AAI mode. Likewise, in the final ECG complex, the A-A escape interval counter does time out, resulting in the generation of an atrial pace event but the succeeding ventricular depolarization for R wave falls within the extended V-V escape interval.

Referring now to FIG. 4, a simplified block diagram of a system that may be implemented entirely or partly in digital logic for practicing the algorithm depicted in FIG. 3 is shown. The block diagram of FIG. 4 operates on the ventricular and atrial sense events (VS and AS), the system clock (CLK) and the X and X+D escape interval data stored in registers in conjunction with pulse width register data to develop the pace initiation and pace enable signals labeled PW (pulse width) and APE, VPE. Those signals are derived from and employed in the systems depicted in FIGS. 1 and 2.

The X interval register 200 and the X+D interval register 202 contain the programmed-in values of the atrial and ventricular pacing escape intervals in the ventricular hysteresis interval described above. Those values are applied to transfer AND gates 206, 208, and 210, which are selectively enabled by transfer (TFR) signals to transfer their contents to the A-A counter 212 and V V counter 214. The A-A counter (when enabled) and V V counter 214 are counted down by applied clock signals, and the count in each counter is monitored by CT=0 decode logic blocks 216 and 218 respectively. The decode logic 216 and 218 provide the atrial pace (AP) and the ventricular pace (VP) signals, respectively, to the pulse width counter/decoder block 220, and also supply the APE and VPE signals to the blocks depicted in FIGS. 1 or 2. The pulse width register 222 loads the pulse width counter 220 with programmed in pulse width data. The count in pulse width counter/decoder block 220 is counted down by the clock signal to provide the desired pulse width of a pacing stimulation pulse upon being triggered by an AP or VP signal.

The remaining components of the block diagram of FIG. 4 control the switching of the X and X+D interval data into the A-A and V-V counters 212 and 214, as well as the enablement of the A-A counter. In the presence of a ventricular sense event, the VS signal is applied as the transfer signal to the transfer and gates 210 to transfer the X+D data into the V-V counter 214. At the same time the VS signal is applied to the set input of flip-flop 226, which responds and provides an enable signal to AND gates 228 and 230 and a trigger signal to one 227 which provides a VS' signal to OR gate 224. OR gate 224 receives the AS and AP signals at two other inputs, and each VS', AS and AP signal is passed through OR gate 224 to AND gate 228 which passes each signal of the enable signal is available from flip-flop 216 at that time. Flip flop 226 is reset by VP signal which in turn disables AND gates 228 and 230.

AND gates 228 and 230 allow the transfer of X interval data from register 200 through transfer AND gates 206 to A-A counter 212 to load the atrial escape interval. This transfer is only accomplished due to the flip flop 226 being set by a preceding VS event and upon the occurrence of an AS or AP event applied to OR gate 224 or upon the simultaneous application of the VS' signal to OR gate 224. Thus, if the flip-flop 226 is set, the presence of any of the AS, VS' or AP signals applied through OR gate 224 pass through AND gate 228 to trigger one shot 232 and produce the transfer signal applied to the transfer AND gate logic 206.

When flip flop 226 is initially set by a VS signal, the pacing mode switches to the AAI mode since that same VS signal processed into VS' signal by one shot 227 is passed by AND gate 228 and one shot 232. Until a VP signal resets flip flop 226, subsequent VS events have no effect on the A-A counter since they do not trigger one shot 227. The setting of the flip-flop 226 also enables AND gate 230 to apply clock signals to the CLK input of A-A counter 212 to enable it to be counted down. As long as flip flop 226 remains set, the pacemaker operates in the AAI mode.

In the event that the V-V counter 214 does count down to zero, the decode logic 218 provides the VP signal as the transfer signal to the transfer AND gates 208 to transfer the X interval data from register 200 to the V-V counter 214. The VP signal is also applied to the reset input of flip flop 226 to switch its state and disable the AND gates 228 and 230. Thus, the A-A counter is disabled from providing an AP output signal until the next VS event sets the flip flop 226 and loads the X interval data into the A-A counter 212. During this time, the pacemaker operates in the VVI mode, and the V-V escape interval is set to the X interval provided from X interval register 200 through transfer AND gates 208. It will be understood that the clocking of data from the various registers into the counters through the transfer AND gates 206, 208 and 210 may be accomplished on the next CLK signal following the TFR signal or concurrently with the TFR signal.

The logic diagram of FIG. 4 thus provides one implementation of the AAI/VVI mode control algorithm depicted in FIGS. 3 and 5. Other implementations may be realized by those skilled in the art.

Figure 6:
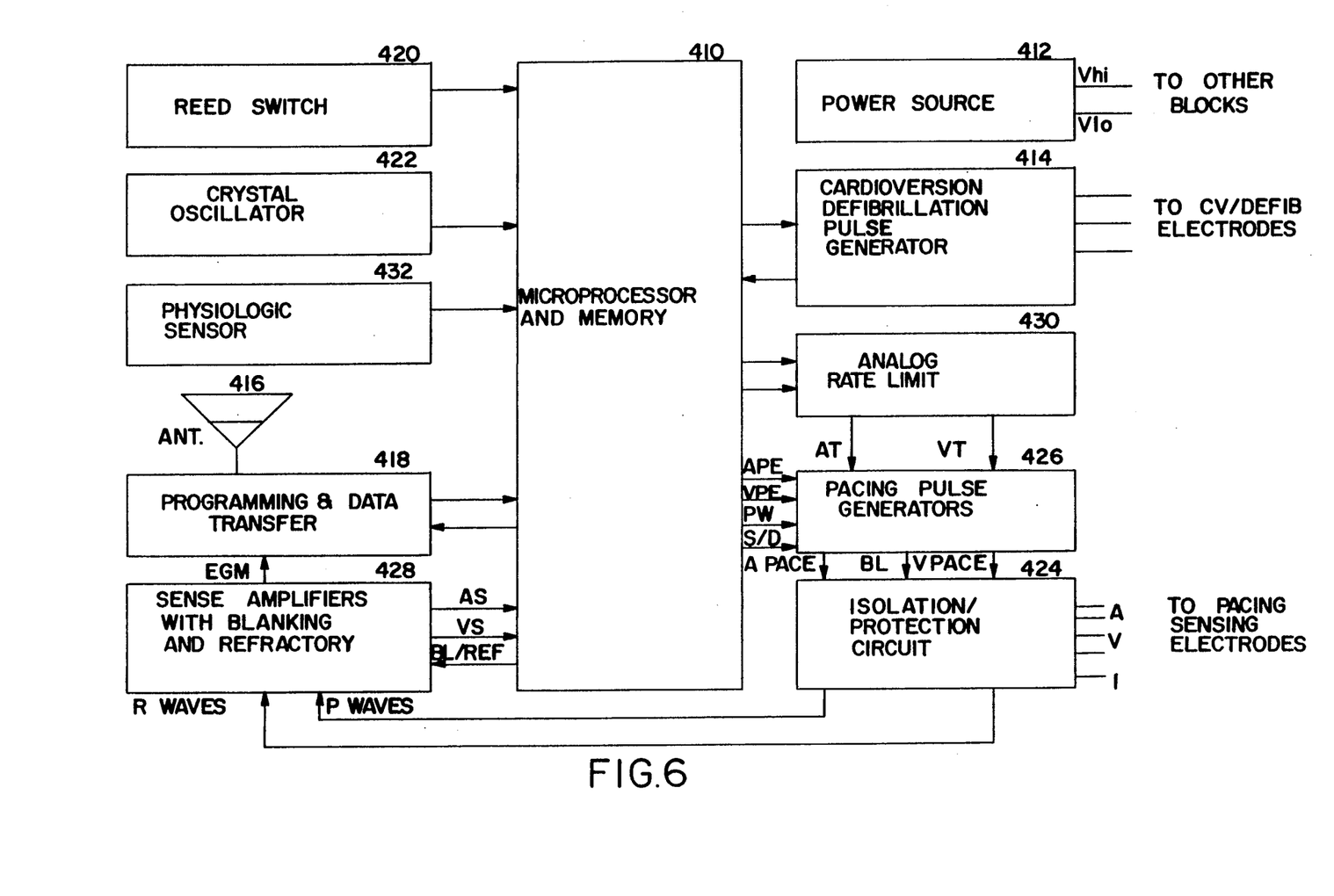
FIG. 6 is a simplified block diagram of a tachyarrhythmia control device in which the invention described with respect to FIGS. 1-5 may be incorporated.

Reference is now made to FIG. 6 which depicts a block diagram of the major components of automatic implantable device for detecting and treating brady and tachyarrhythmias. It is contemplated that such a device would be implemented in analog and digital microcircuits under the control of a central microprocessor/memory block 410 powered by high (for cardioversion and defibrillation) and low (for the remaining circuitry on pacing therapies) power sources in block 412. The high power pulse generator block 414 would include the cardioversion/defibrillation pulse generator circuitry coupled by output terminals to two or more cardioversion/defibrillation electrodes to apply synchronized cardioversion or unsynchronized defibrillation shocks to the electrodes situated in or about the heart in a manner well known in the art. The bradycardia pacing blocks of FIGS. 1 or 2 and the AAI/VVI mode switching algorithm and logic block diagram of FIG. 3 and 5 would be incorporated into this device.

It is contemplated that the implantable device depicted in FIG. 6 would function under the control of a resident operating program or software retained in memory within the microprocessor/memory block 410 and would be programmable by an external programmer/receiver (not illustrated in FIG. 6) communicating with the implanted device by radio frequency energy received o transmitted by antenna 416 under the control of the programming and data transmission block 418 and reed switch 420 which is responsive to an external magnet. The programming and data transmitting block 418 would be capable of receiving programming instructions and directing them to the memory within microprocessor/memory block 410 as well as transmitting data stored within the memory block 410 as well as an electrogram representing the patient s atrial and ventricular activity in a manner well known in the pacing art.

The timing of all processing functions, including the determination of atrial and ventricular escape intervals, is controlled by system clocks within microprocessor/memory 410 driven by crystal oscillator 422 in a manner well known in the prior art of implantable digital pacemakers and as described above.

The cardiac signal processing blocks of FIG. 6 include the isolation/protection or interface block 424 which operates to direct atrial and/or ventricular pacing stimuli from the pacing pulse generator block 426 to respective atrial and ventricular output terminals which in turn are coupled through the pacing leads to unipolar or bipolar pacing electrodes situated in or near the atrium and ventricle of the heart as shown in FIGS. 1 and 2, respectively. In addition, the interface 424 (when unblanked) couples the near-field and far field atrial and ventricular electrograms to the sense amplifier block 428. Interface 424 is blanked or prevented from passing any signals picked up on the atrial and ventricular pacing/sensing electrodes to the sense amplifier block 428 during short blanking intervals following the delivery of an atrial or ventricular pacing stimulus in a fashion well known in the pacing art.

The indifferent plate electrode of FIG. 1 is coupled to the interface circuit 424 which is used in conjunction with the bipolar pacing/sensing electrodes to provide far field, unipolar signals to the sense amplifier 428 in the manner described in my above referenced '133 application. The plate electrode may be one of the cardioversion/defibrillation electrodes, the case of the pulse generator or a separate electrode on or attached to one of the lead bodies.

Furthermore, the interface 424 disconnects or shorts out the pacing/sensing electrodes during the delivery and for a short period after the delivery of a cardioversion/defibrillation shock by application of a control signal to the interface 424 by the cardioversion/defibrillation pulse generator block 414.

The P-wave and R-wave signals transmitted through the interface 424 to the sense amplifiers 428 are amplified and shaped to generate the near field and far-field atrial and ventricular signals AS and VS, respectively, which are conducted to microprocessor/memory 410 in order to derive the atrial and ventricular cycle lengths, the AV delay interval, and other intervals and rates described hereinbefore to perform the inventive functions of the device. A further signal from a physiologic sensor 432 representative of cardiac or patient activity may also be applied to the microprocessor/memory 410 in order to control the bradyarrhythmia pacing rate in the DDDR or other rate responsive mode of operation (if it is programmed to do so) and to augment detection of tachyarrhythmias.

The microprocessor/memory 410 responds to atrial and ventricular AS and VS signals by generating appropriate atrial and ventricular refractory and blanking intervals which are in turn applied to the sense amplifier block 428 during certain windows of time following each respective AS and VS signal in a fashion well known in the pacing art.

It is contemplated that the system depicted in FIG. 6 may be programmed to operate in any of the known bradycardia single or dual chamber pacing modes and in the AAI/VVI modes of the present invention. In certain of these modes the signal from the physiologic sensor 432 may be employed to modify the atrial and ventricular escape intervals to allow for a certain range of atrial and ventricular pacing depending upon the level of the patient's activity in a fashion well known in the bradycardia pacing art. Suffice it to say, that atrial and ventricular escape intervals established in memory are compared against the atrial and ventricular cycle lengths encountered in the patient and, if a bradycardia condition exists, the microprocessor/memory 410 applies atrial and ventricular pace trigger signals AT and VT through analog rate limiter block 430 to the pacing pulse generator 426 which responds by developing the respective AP and/or VP signals as described hereinbefore. Analog rate limiter 430 operates to limit atrial and ventricular pacing rates to a safe high rate to protect against component runaway conditions and to effect an appropriate upper rate behavior (in synchronous modes not involving the present invention) in the event that the spontaneous atrial rate exceeds the programmed upper rate limit.

Although presently preferred embodiments of the invention have been described, it will be apparent from that description to those skilled in the field to which the invention pertains, that variations of the present embodiments may be implemented without departing from the principles of the invention. Further, as technological advances are made, for example, in developing practical small size, low-cost high voltage components, similar to the advances in the semiconductor field, the principles of the invention may be applied directly to a "universal" implantable device for performing an all purpose cardiac treatment function.

Accordingly, it is intended that the invention be limited not by the structural or functional elements of the described embodiment, but only as set out in the appended claims.

What I claim is:

1. In a cardiac pacemaker capable of being operated in at least two pacing modes the improvement in switching modes between a first demand mode involving the sensing of natural depolarizations from and stimulation of a first chamber of a patient's heart and a second demand mode involving the sensing of natural depolarizations from and the stimulation of a second chamber of the patient's heart comprising:

first sensing means for sensing natural depolarizations of the first chamber of the heart and providing first sense signals;

second sensing means for sensing natural depolarizations of the second chamber of the heart and providing second sense signals;

means for providing stimulation pulses to said first chamber of the heart after a first predetermined escape interval has elapsed from a preceding first sense signal or first stimulation pulse;

means for providing stimulation pulse to said second chamber of the heart after a second predetermined escape interval has elapsed from a preceding second sense signal or second stimulation pulse; and mode switching means for operating said first chamber stimulation pulse providing means in the presence of a second sense signal and for operating said second chamber stimulation pulse providing means in the absence of second sense signals recurring within said second escape interval.

2. The cardiac pacemaker of claim 1 wherein:

said first chamber stimulation pulse providing means further comprises first escape interval timing means responsive to said first sense signal for providing said first chamber stimulation pulse after said first escape interval elapses in the absence of an intervening first sense signal;

said second chamber stimulation pulse providing means further comprises second escape interval timing means responsive to said second sense signal for providing said second chamber stimulation pulse after said second escape interval elapses in the absence of an intervening second sense signal; and said mode switching means further comprises means for making said second escape interval egual to said first escape interval during the time that said second stimulation pulse providing means is operating and for making said second escape interval greater than said first escape interval at times when said first stimulation pulse providing means is operational.

3. A method of automatically switching pacing modes in a cardiac pacemaker between atrial demand and ventricular demand modes comprising:

sensing atrial depolarizations of the heart and providing atrial sense signals;

sensing ventricular depolarizations of the heart and providing ventricular sense signals;

timing a first ventricular escape interval from the occurrence of a ventricular sense signal and a second ventricular escape interval from the generation of a ventricular pace event signal;

timing an atrial escape interval from the occurrence of an atrial sense signal and the generation of an atrial pace event signal;

generating a ventricular pace event signal at the end of either said first or said second ventricular escape intervals;

pacing the ventricle of the heart each time a ventricular pace event signal is generated;

pacing the atrium of the heart each time an atrial pace event signal is generated and as long as no ventricular pace events are generated; and switching from the pacing of the atrium to the pacing of the ventricle each time that a ventricular pace event signal is generated.

4. In a cardiac pacemaker capable of being operated in at least two pacing modes, the improvement in switching modes between an AAI mode involving the sensing of natural atrial depolarizations and pacing the atria on demand and a VVI mode involving the sensing of ventricular depolarizations and pacing the ventricle of the patient's heart on demand comprising:

atrial sensing means for sensing natural atrial depolarizations and providing atrial sense signals;

ventricular sensing means for sensing natural ventricular depolarizations and providing ventricular sense signals;

atrial pacing means for providing pacing pulses to said atria after an atrial escape interval has elapsed from a preceding atrial sense signal or atrial pacing pulse;

ventricular pacing means for providing pacing pulse to said ventricle after a ventricular escape interval has elapsed from a preceding ventricular sense signal or ventricular pace pulse; and mode switching means for operating said atrial pacing means in the AAI mode upon the occurrence of a ventricular sense signal and for operating said ventricular pace means in the VVI mode in the absence of ventricular sense signals recurring within said ventricular escape interval.

5. The cardiac pacemaker of claim 4 wherein:

said atrial pacing means further comprises atrial escape interval timing means responsive to said atrial sense signal for providing said atrial pace pulse after said atrial escape interval elapses in the absence of an intervening atrial sense signal;

said ventricular pacing means further comprises ventricular escape interval timing means responsive to said ventricular sense signal for providing said ventricular pace pulse after said ventricular escape interval elapses in the absence of an intervening ventricular sense signal; and said mode switching means further comprises means for making said ventricular escape interval egual to said atrial escape interval during the time that said ventricular pacing means is operating and for making said ventricular escape interval longer than said atrial escape interval at times when said atrial pacing means is operational.

6. Apparatus for automatically switching pacing modes in a cardiac pacemaker between atrial demand and ventricular demand modes comprising:

means for sensing atrial depolarizations of the heart and providing atrial sense signals;

means for sensing ventricular depolarizations of the heart and providing ventricular sense signals;

means for timing a first ventricular escape interval from the occurrence of a ventricular sense signal and a second ventricular escape interval from the generation of a ventricular pace event signal;

means for generating an atrial pace event signal at the end of an atrial escape interval and for timing said atrial escape interval from the occurrence of a ventricular sense signal, an atrial sense signal, and the generation of an atrial pace event signal;

means for generating a ventricular pace event signal at the end of either said first or said second ventricular escape intervals;

means for pacing the ventricle of the heart each time a ventricular pace event signal is generated;

means for pacing the atrium of the heart each time an atrial pace event signal is generated and as long as no ventricular pace events are generated; and means for switching from the pacing of the atrium to the pacing of the ventricle each time that a ventricular pace event signal is generated.

7. In a tachycardia control system comprising a pacemaker/cardioverter/defibrillator for providing pacing energy antitachycardia therapies, cardioversion energy antitachycardia therapies and defibrillation energy therapies as required to convert a tachyarrhythmia to a normal rhythm, the improvement providing bradycardia pacing support therapies in the absence of a detected tachyarrhythmia comprising:

means for providing AAI or VVI pacing therapies to the patient's heart; and mode switching means for operating the AAI mode and disabling the VVI mode in the presence of certain ventricular heart rhythms and operating in the VVI mode and disabling the AAI mode in the absence of certain ventricular heart rhythms.

8. The system of claim 7 further comprising:

means for sensing natural depolarizations of the atrium of the heart and providing atrial sense signals;

means for sensing natural depolarizations of the ventricle of the heart and providing ventricular sense signals;

means for providing atrial stimulation pulses to said atrium after an atrial escape interval has elapsed from a preceding atrial sense signal or stimulation pulse;

means for providing ventricular stimulation pulse to said ventricle after a ventricular escape interval has elapsed from a preceding ventricular sense signal or stimulation pulse; and wherein said mode switching means switches mode from said VVI mode to said AAI mode by commencing operation of said atrium stimulation pulse providing means when a ventricular sense signal occurs during said VVI mode and switches from said AAI mode to said VVI mode by commencing operation of said stimulation pulse providing means in the absence of ventricular signals recurring within said ventricular escape interval.

9. In a tachycardia control system comprising a pacemaker/cardioverter/defibrillator for providing pacing energy antitachycardia therapies, cardioversion energy antitachycardia therapies and defibrillation energy therapies as required to convert a tachyarrhythmia to a normal rhythm, the improvement providing bradycardia pacing support therapies in the absence of a detected tachyarrhythmia comprising:

sensing atrial depolarizations of the heart and providing atrial sense signals;

sensing ventricular depolarizations of the heart and providing ventricular sense signals;

timing a first ventricular escape interval from the occurrence of a ventricular sense signal and a second ventricular escape interval from the generation of a ventricular pace event signal;

timing an atrial escape interval from the occurrence of an atrial sense signal and the generation of an atrial pace event signal;

generating a ventricular pace event signal at the end of either said first or said second ventricular escape intervals;

pacing the ventricle of the heart each time a ventricular pace event signal is generated;

pacing the atrium of the heart each time an atrial pace event signal is generated and as long as no ventricular pace events are generated; and switching from the pacing of the atrium to the pacing of the ventricle each time that a ventricular pace event signal is generated.

10. A method for operating a pacemaker to provide demand pacing at a lower rate in either the atrium or the ventricle, depending upon the presence or absence of ventricular sensed events recurring within a predetermined ventricular escape interval, comprising the steps of:

providing atrial demand pacing at a predetermined atrial lower rate escape interval as long as ventricular events are sensed within the ventricular escape interval; and switching modes to provide ventricular demand pacing and inhibit atrial demand pacing in the event that the ventricular escape interval times out without an intervening sensed ventricular event.

11. The method of claim 10 further comprising the step of:

switching from the ventricular demand pacing to atrial demand on the detection of any ventricular event within the ventricular escape interval.

12. The method of claim 10 or claim 11 further comprising the steps of:

continuing to time out the ventricular escape intervals while operating in the atrial demand mode; and halting the timing out of the atrial escape intervals while operating in the ventricular demand mode.

13. The method of claim 10 or 11 further comprising the steps of:

prolonging the ventricular escape interval, while operating in the atrial demand mode, to bias the continued operation of the pacing system in favor of the atrial demand mode, while assuring that ventricular pacing occurs should an excessive time pass with no ventricular activity having occurred.

14. Apparatus for operating a pacemaker to provide demand pacing at a lower rate in either the atrium or the ventricle, depending upon the presence or absence of ventricular sensed events recurring within a predetermined ventricular escape interval, comprising:

means for providing atrial demand pacing at a predetermined atrial lower rate escape interval as long as ventricular events are sensed within the ventricular escape interval; and means for switching modes to provide ventricular demand pacing and inhibit atrial demand pacing in the event that the ventricular escape interval times out without an intervening sensed ventricular event.

15. The apparatus of claim 14 further comprising:

means for switching from the ventricular demand pacing to atrial demand pacing on the detection of any ventricular event within the ventricular escape interval.

16. The apparatus of claim 14 or claim 15 further comprising:

means for continuing to time out the ventricular escape intervals while operating in the atrial demand mode; and means for halting the timing out of the atrial escape intervals while operating in the ventricular demand mode.

17. The apparatus of claim 14 or 15 further comprising:

means for prolonging the ventricular escape interval, while operating in the atrial demand mode, to bias the continued operation of the pacing system in favor of the atrial demand mode, while assuring that ventricular pacing occurs should an excessive time pass with no ventricular activity having occurred.

* * * * *